United States Patent [19]

Bluestein et al.

[11] Patent Number: 4,780,423

[45] Date of Patent: Oct. 25, 1988

[54] HETEROGENEOUS FLUORESCENCE ASSAYS USING CONTROLLED PORE GLASS PARTICLES

[75] Inventors: Barry I. Bluestein, Mansfield, Mass.; A. Judy Famulare, Dumont; Thomas E. Worthy, Waldwick, both of N.J.

[73] Assignee: Ciba Corning Diagnostics Corp., Medfield, Mass.

[21] Appl. No.: 939,903

[22] Filed: Dec. 9, 1986

[51] Int. Cl.$^4$ .................................... G01N 33/552
[52] U.S. Cl. ................................ 436/527; 436/800
[58] Field of Search ............................ 436/527, 800

[56] References Cited

U.S. PATENT DOCUMENTS

| | | | |
|---|---|---|---|
| 4,197,361 | 4/1980 | Hoff | 436/800 X |
| 4,280,992 | 7/1981 | Sugiura | 436/527 |
| 4,297,337 | 10/1981 | Mansfield | 436/527 |
| 4,425,438 | 1/1984 | Bauman | 436/527 |
| 4,680,120 | 7/1987 | Ramsden | 436/527 X |

*Primary Examiner*—Sidney Marantz
*Attorney, Agent, or Firm*—Daniel Reitenbach

[57] ABSTRACT

Improved heterogeneous fluorescence assays are provided which employ solid supports comprising controlled pore glass particles which are substantially transparent at both the wavelength used to excite the fluorescent probe used in the assay and at the emission wavelength of the probe. The assays achieve sensitivities comparable to those achieved with radioimmunoassays without the need to concentrate the particles prior to the fluorescent measurement as in prior art heterogeneous fluorescence assays employing other types of solid supports.

7 Claims, 2 Drawing Sheets

HETEROGENEOUS FLUORESCENCE ASSAYS USING CONTROLLED PORE GLASS PARTICLES

BACKGROUND OF THE INVENTION

1. Field of the Invention

This invention relates to improved solid supports for use in heterogeneous fluorescence assays employing a ligand and a specific binding partner to the ligand and, in particular, to improved solid supports for use in fluorescence immunoassays (FIA).

2. Description of the Prior Art

One of the major advances in the clinical laboratory over the past 25 years has been the employment of antibodies to measure extremely small quantities of analytes in biological samples. These immunoassays are characterized by specificities and sensitivities which were unachievable with prior techniques.

The first immunoassay was described in 1959 by Berson and Yalow (Berson, S.A. and Yalow, R.S., Quantitative aspects of the reaction between insulin and insulin binding antibody. J. CLIN INVEST. 38:1996–2016, 1959) and utilized radioactive insulin as a "tracer" probe in a competitive antigen-antibody immunologic reaction. A variety of permutations as to how immunoassays are practiced including the use of radiolabeled antibodies in an immunometric (IRMA) format rather than radiolabeled antigen in a competitive binding format have developed since Berson's and Yalow's initial work.

The use of radiolabeled substances in immunoassays has limited the sites in the clinical laboratory where these assays could be performed due to the biological hazards associated with radioactivity. Also, the need to properly dispose of the radioactive waste materials resulting from these assays has increased their cost. Further, radioisotopes have limited life times as assay reagents due to isotopic decay. As a consequence, there have been continuing efforts to find non-radioactive "tracers" to substitute for radioisotopes in immunoassays. Unfortunately, it has been difficult to develop non-radioactive immunoassays which match the high sensitivity and specificity achieved with radioimmunoassays.

One type of non-radioactive tracer which has been employed in immunoassays with some success and with which the present invention is concerned, is the fluorescent tracer. These tracers have been used in immunoassays since the early 1960's. Reviews of the progress made to date with these tracers can be found in, for example, Cobb, M. and Gotcher, S., Fluorescence immunoassay in the clinical laboratory. AMERICAN J. MED. TECH. 48(8) 671–677, 1982.; Hemmila, I., Fluoroimmunoassays and immunofluorometric assays. CLIN. CHEM. 31(3): 359–370, 1985.; and Nakamura, R.M., Advances in analytical fluorescence immunoassays—methods and clinical applications. In: Nakamura, R.(ed.), CURRENT TRENDS IN CLINICAL LABORATORY ASSAYS, Scripps Research Foundation, La Jolla, Calif., pp. 33–59, 1982.

A major problem with fluorescence immunoassays has been interference due to endogenous serum components. Depending on the particular tracer used, this interference can take the form of absorption ("quenching") of the tracer's output or high background at the wavelength being detected. Depending on the excitation and emission wavelengths of the tracer, serum constituents that may interfere include: proteins, albumin-bilirubin complexes, hemoglobin and vitamins.

The result of this interference by serum components is a loss in assay sensitivity. This loss in sensitivity has tended to limit the application of fluorescence immunoassays to the detection of compounds present in relatively high concentration in the blood, such as, immunoglobulins, the proteins making up complement (C reactive protein) and drugs.

The interference caused by serum components can be reduced or eliminated by removing the interfering components either before or after the immunologic reaction is run. If removed or diluted out before the immunologic reaction takes place, the assay may be run in a "homogeneous" mode, wherein the output of the system is obtained without separating bound and unbound tracer. In general, fluorescence immunoassays employing a homogeneous format have tended to have low sensitivities as a result of the high sample dilutions needed to reduce background fluorescence to acceptable levels.

Heterogeneous formats have also been employed in fluorescence immunoassays. In this mode, the interfering substances are removed after the immunologic reaction takes place by separating the antigen-antibody complex from the reaction mixture. This format generally involves washing the antigen-antibody complex and then resuspending it in solution prior to obtaining an output reading. In order to be able to perform the separation, washing and measurement steps conveniently, the antigen-antibody complex is preferably formed on a solid support. The present invention is directed to providing improved solid supports for use in heterogeneous fluorescence immunoassays, as well as in other types of heterogeneous fluorescence assays in which the presence or concentration of a ligand is determined through the use of a specific binding partner for the ligand.

Prior to the present invention, various solid supports have been employed in heterogeneous fluorescence immunoassays. For example, U.S. Pat. Nos. 4,201,763 (1980) and 4,295,199 (1981), assigned to Bio-rad Laboratories, Inc., Richmond, Calif., describe the use of 0.1-10 micron hydrophilic polymer particles, in particular, 5 micron polyacrylamide beads, to perform heterogeneous fluorescence immunoassays. In this system, after washing, the solid phase antigen-antibody complex is reconstituted into suspension and read in a conventional 90 degree fluorometer. In practice, the Bio-Rad system has been found not to have the required sensitivity to measure small concentrations of analytes and has been restricted primarily to the measurement of immunoglobulins in high concentrations.

Heterogeneous fluorescence immunoassays have also been performed by immobilizing antibodies on flat polymeric surfaces, e.g., surfaces made of polymethylmethacrylate or cellulose nitrate. See Tsay Y.G., Wilson, L., Keefe, E., Quantitation of serum gentamicin concentration by solid phase immunofluorescence method. CLIN.CHEM. 26:1610–1612, 1980. This system has been sold commercially by International Diagnostics, Santa Clara, Calif., under the trade name FIAX-StiQ.

Unlike the Bio-Rad system described above, the FIAX-StiQ system uses front face (zero degree) epifluorometry, rather than conventional 90 degree fluorometry. Detecting the fluorescent output of the probe along the same axis used to excite the probe can produce increased optical sensitivities, as demonstrated below in connection with the preferred embodiments of the present invention. In the FIAX-StiQ system, however, because of its use of a flat surface, full advantage of the front face orientation has not been achieved. Specifically, the FIAX-StiQ system produces a relatively limited utilizable signal due to the low surface area:volume ratio inherent to a flat surface. Only the portion of the flat surface illuminated by the incident beam can produce a fluorescent output signal. Since only a limited number of "tracer" probes can be in the illuminated area due to its limited surface area, the obtained signals are small and lack sensitivity to measure low analyte concentrations. In practice, the FIAX-StiQ system has been used to measure drugs and patient analytes present in high concentration.

Magnetic solid supports have also been used in heterogeneous fluorescence immunoassays. Thus, Pourfarzaneh et al., in an article entitled "Cortisol directly determined in serum by fluoroimmunoassay with magnetizable solid phase," CLIN. CHEM. 26:730-733 (1980), describe the use of magnetizable solid phase cellulose-iron oxide particles to which antibody has been coupled in a fluorescence immunoassay. Unfortunately, these particles are black body absorbers capable of absorbing all the exciting and fluorescent light employed in conventional fluorometry. As a consequence, Pourfarzaneh et al. were forced to add an additional elution step, wherein the fluorescent probe was eluted from the antibody prior to the fluorescence measurement, in order to make their system work.

In addition to the foregoing, Pandex Laboratories, Inc., Mundelein, Illinois, has commercialized a heterogeneous fluorescence immunoassay which it has called "particle concentration fluorescence immunoassay" (PCFIA). See European Patent Publication No. 124,050 (1984) and Jolley et al., Particle Concentration Fluorescence Immunoassay (PCFIA): A New Rapid Immunoassay Technique with High Sensitivity. JOURNAL OF IMMUNOLOGICAL METHODS, 67:21-35 (1984).

This system utilizes front face epifluorescence and polystyrene latex particles having a diameter of 10 microns or less to which antigen or antibody has been chemically coupled. Particles of these sizes will generally stay in suspension for the duration of the immunologic reaction. After the immunologic reaction has been completed, the particles are washed and concentrated by vacuum microfiltration through a membrane filter, e.g., a cellulose acetate or other polymeric filter. Front face epifluorometry is then performed on the concentrated particles. Background due to stray light and light scattered from particles and endogenous fluorescence due to the filter membranes is corrected for each sample by inclusion of a small amount of reference particles sampled at different wavelengths then the "tracer" fluorophore.

According to Pandex, concentrating the particles before measuring their fluorescence results in an increase in sensitivity by increasing the number of "tracer" fluorophores per unit area available for excitation by the incident light beam. As demonstrated below, by using the solid supports of the present invention, such concentration of the solid phase to achieve enhanced sensitivities is not necessary.

SUMMARY OF THE INVENTION

In view of the foregoing state of the art, it is an object of the present invention to provide improved solid supports for use in heterogeneous fluorescence assays in which the presence or concentration of a ligand is determined through the use of a specific binding partner for the ligand. More particularly, it is an object of the invention to provide such improved solid supports for use in heterogeneous fluorescence immunoassays. Even more particularly, it is an object of the invention to provide improved solid supports for heterogeneous fluorescence immunoassays which allow such assays to achieve sensitivities comparable to those achieved with radioimmunoassays. It is an additional object of the invention to provide such sensitivities without the need for elution of the fluorescent probe from the antigen-antibody complex or the need for concentrating the solid-support prior to making the fluorescence measurement.

To achieve the foregoing and other objects, the invention provides improved heterogeneous fluorescence assays employing solid supports which comprise controlled pore glass particles which are substantially transparent at both the wavelength used to excite the fluorescent probe used in the assay and at the emission wavelength of the probe and which have the properties of: (1) a mean pore size of between about 400 angstroms and about 800 angstroms; (2) a mean diameter of between about 0.7 microns and about 3.0 microns; and (3) a mean surface area to mass ratio of at least 40 meter$^2$/gm, and preferably between about 40 meter$^2$/gm and about 125 meter$^2$/gm.

In certain preferred embodiments, the controlled pore glass particles are composed of borosilicate glass, have a mean pore size of about 550 angstroms, a mean diameter of about 1.5 microns, and a mean surface area to mass ratio of between about 40 meter$^2$/gm and about 100 meter$^2$/gm. In other preferred embodiments, front face epifluorometry, as opposed to conventional 90 degree fluorometry, is performed with the controlled pore glass particles. When performed in this way, the improved assays of the present invention achieve sensitivities equivalent to those achieved with radioimmunoassays. Moreover, these sensitivities are achieved without the need to concentrate the particles prior to making the fluorescence measurement.

DESCRIPTION OF THE PREFERRED EMBODIMENTS

Figure 1:
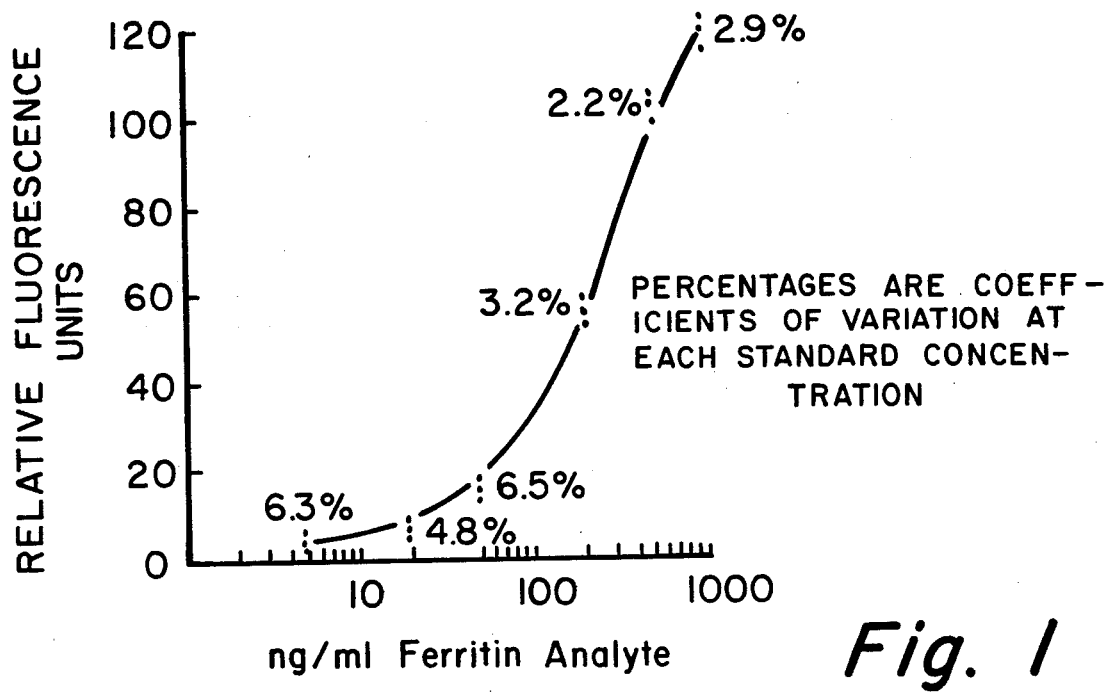
FIG. 1 is a standard curve for the analyte ferritin prepared using a 2-site immunometric fluorescence immunoassay employing the solid supports of the present invention.
Figure 3:
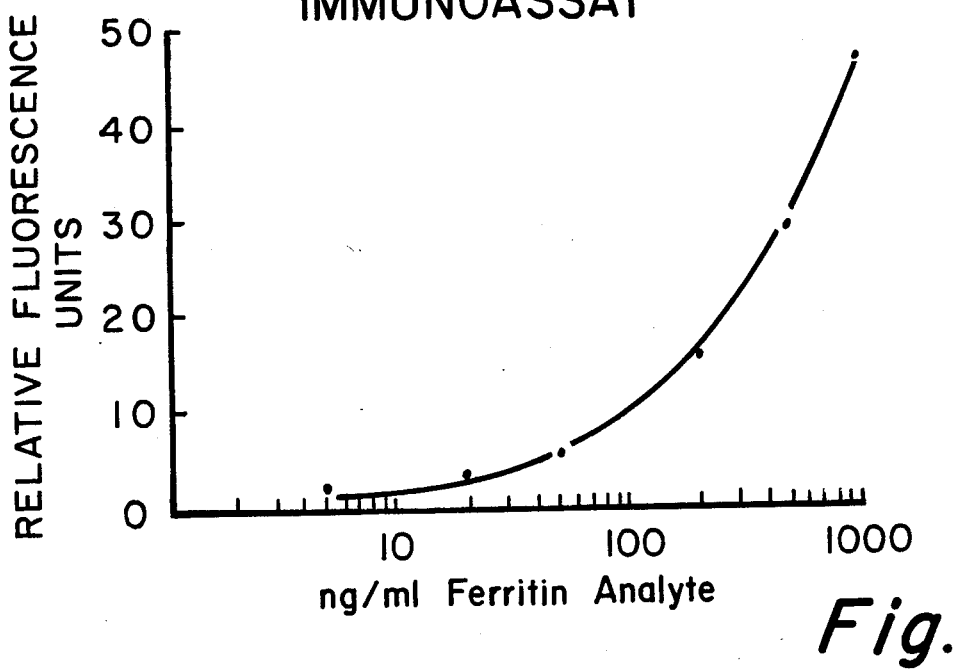
FIG. 3 is a standard curve for the analyte ferritin prepared using a 2-site immunometric fluorescence immunoassay employing MAGIC particles (iron oxide magnetizable paramagnetic particles available from Ciba Corning Diagnostic Corp., Medfield, Mass.) as the solid support.

As described above, the present invention relates to heterogeneous fluorescence assays performed with controlled pore glass (CPG) particles. The invention can be used in all types of fluorescence assays which employ a ligand and a specific binding partner to the ligand, including, without limitation, assays in which the ligand or the specific binding partner is an immunoglobulin, a DNA probe, a receptor tissue protein, a hormone, a drug, or the like. Prior to the present invention, controlled pore glass particles have been used in radioimmunoassays, but not in fluorescence assays.

The controlled pore glass particles suitable for use with the present invention are generally of the same types as those which have been used in the past with radioimmunoassays. Thus, the particles should have a mean diameter of between about 0.7 microns and about 3.0 microns so that the particles will remain in suspension during the immunologic reaction. Similarly, the particles should have a mean pore size of between about 400 angstroms and about 800 angstroms so that the various reactants (ligands, specific binding partners, coupling agents, etc.) will readily pass into and out of the pores. Also, the particles should have a mean surface area to mass ratio of at least 40 meter$^2$/gm so that large amounts of ligand or specific binding partner, depending on the assay format, can be coupled to the particles. A discussion of controlled pore glass particles in the context of radioimmunoassays, including sources of such particles and methods for coupling materials to the particles, appears in Vann et al., U.S. Pat. No. 3,975,511, and Baker et al., U.S. Pat. No. 4,052,010, and the references referred to in those patents, the pertinent portions of which are incorporated herein by reference.

In addition to the foregoing, as illustrated in Example 6, infra, the controlled pore glass particles should be substantially transparent at the excitation and emission wavelengths used in the assay. Although not wishing to be bound by any particular theory of operation, it is believed that the enhanced sensitivities achieved with CPG particles, as compared to polymeric particles, e.g., latex particles, is due to a combination of the greater surface area to mass ratios exhibited by CPG particles and the fact that probe molecules located within the pores of CPG particles can contribute to the fluorescence signal since excitation and emission light can pass through the particles.

Particularly suitable CPG particles for use with the present invention are those sold by Ciba Corning Diagnostics Corp., Medfield, Mass., and presently being used in its commercial IMMOPHASE radioimmunoassay kits. These CPG particles are used in the examples presented below. The particles are composed of borosilicate glass, have a mean pore size of about 550 angstroms, a mean diameter of about 1.5 microns, and a mean surface area to mass ratio of between about 40 meter$^2$/gm and about 100 meter$^2$/gm.

The controlled pore glass particles of the present invention can be used to perform assays with essentially any fluorescent probe now known or subsequently developed. Similarly, the invention can be used to perform assays for essentially any ligand whose absorption and emission spectrum, and that of its specific binding partner, will not interfere with the fluorescent behavior of the probe. Along these same lines, the invention can be used with heterogeneous assays having a variety of assay configurations now known or subsequently developed.

For example, as illustrated in Example 3, infra, the CPG particles can be used in a classical immunoassay employing a competitive binding configuration wherein antibody is bound to the particles, e.g., through an organosilane coupling, and the antigen in a sample competes with fluorescent-labelled antigen for antibody binding sites. Similarly, as illustrated in Examples 1-5, infra, an immunometric, two-site configuration can be used wherein antibody bound to CPG particles is reacted with antigen in a sample and a second, fluorescent-labelled antibody is reacted with the bound antigen.

Other heterogeneous configurations are discussed in the FIA review articles, discussed above, as well as in European Patent Publication No. 124,050, the pertinent portions of which are incorporated herein by reference. As will be evident to persons skilled in the art, the present invention is as equally applicable to these assay configurations as it is to the configurations illustrated in the examples. Similarly, the review articles describe various fluorescent probes which can be used in fluorescence immunoassays. Again, the use of these and other probes in connection with the present invention will be evident to persons skilled in the art in view of the present disclosure.

Without intending to limit it in any manner, the invention will be further described and illustrated by the following examples.

EXAMPLE 1

Comparison With RIA

This example compares the sensitivity of a heterogeneous fluorescence immunoassay (FIA) employing the solid supports of the present invention with a commercially available radioimmunoassay (RIA).

The analyte ferritin, which is involved in iron storage in the body, was used for the comparison. This analyte has a broad dynamic clinical range in serum ranging from $1 \times 10^{-11}$ molar to $2 \times 10^{-9}$ molar, the low end of this range corresponding to the lowest concentration detection level necessary for all clinical analytes which are currently tested routinely.

The radioimmunoassay was performed using an IMMOPHASE radioimmunoassay kit manufactured by Ciba Corning Diagnostics Corp., Medfield, Mass. (Product No. 474244). This kit employs an immunometric, two-site assay configuration, wherein the sample, a radiolabeled anti-ferritin antibody, and an anti-ferritin antibody coupled to CPG glass through organosilane linkages are incubated together, the solid phase is removed from the mixture and washed, and then the amount of radioactive tracer which has become bound to the solid phase is measured. The radioimmunoassay was performed following the instructions for the commercial kit and included a 2.5 hour incubation period.

The fluorescence immunoassay of the present invention employed the same immunometric, two-site assay configuration as the radioimmunoassay. In place of the radiolabeled anti-ferritin antibody, a fluorescein labelled antibody was used. Specifically, following standard procedures, fluorescein was derivatized to DEAE AffiGEl Blue, (Biorad Labs, Richmond, Calif.), purified anti-ferritin antibodies using fluorescein isothiocyanate (FITC). See *Fluorescent Antibody Techniques and Their Applications*, A. Kamamura, ed., University Park Press, Baltimore, Md., 1969, pages 33-50, for a description of the derivatization process.

The solid phase reagent employed in the FIA was the same as that employed in the RIA. Specifically, it comprised controlled pore borosilicate glass particles to which anti-ferritin antibody had been covalently coupled through organosilane linkages. See Eaton, D. L., *Advances in Experimental Medicine and Biology*, 42:241 (1974), Plenum Press, New York, and U.S. Pat. Nos. 3,652,761, 3,790,475, and 3,792,987 for a description of the process used to prepare the CPG particles, and see Weetall, H. H., *Advances in Experimental Medicine and Biology*, 42:191 (1974), Plenum Press, New York, and Weetall, H. H., "Covalent Coupling Methods for Inorganic Support Materials," *Methods in Enzymology*, 44:134–148 (1976) for a description of the coupling process. These particles are sold commercially under Part No. 474241 by Ciba Corning Diagnostics Corp., Medfield, Mass. as part of the IMMOPHASE ferritin kit.

The particles had a mean diameter of 1.5 microns and etched pores having a mean pore size of 550 angstroms. The bulk density of the porous borosilicate glass particles was between 0.4 grams/milliliter to 0.8 grams/milliliter. The mean surface area per gram of particles was between about 40 meter$^2$ and about 100 meter$^2$, which corresponds to a calculated mean surface area to volume ratio for the particles of between about 16 meter$^2$/milliliter and about 80 meter$^2$/milliliter.

The fluorescence immunoassay was run in a 2 step format. 500 microliters (ul) of solid phase antibody was first incubated with 200 ul of sample standards containing 0, 5, 20, 50, 200, 500 and 1000 nanograms/milliliter (ng/ml) of ferritin for 1 hour at room temperature in 12×75 mm plastic tubes. Following incubation, samples were washed twice with 2 ml of Dulbeccos phosphate buffered saline (PBS). Separation of bound and free sample was effected by centrifugation at 3000 rpm for 10 minutes. Supernatants were aspirated and a 1:10 dilution of the fluorescein derivatized anti-ferritin antibody described above in 0.1% bovine serum albumin (BSA)-PBS buffer was added to each tube and mixed with the sedimented CPG particles. Following incubation for an additional 1 hour, a second series of washings were conducted as above and pellets reconstituted in 200 ul of PBS.

The reconstituted pellets were transferred individually with Pasteur pipettes to 96 well format polystyrene microtiter plates (Corning Glass Works, Corning, N.Y.) and epifluorescence measurements of the suspensions were immediately taken. Readings were zeroed at the 0 ng/ml standard to compensate for scatter due to the solid phase CPG and non-specific fluorescence due to non-immunologically adsorbed fluorophore.

The epifluorescence measurements were performed utilizing an Olympus fluorescent microscope (Model BHS) fitted with a BH—RFL—W epifluorescence assembly. At the top of the microscope where a camera assembly is normally placed, a Zeiss photomultiplier tube was mated to the Olympus microscope. Electronics and data output were supplied by a Zeiss model PMI-2 controller. Optics included an Olympus EY 455 ultraviolet filter and 490 nm interference filter (IF-490) in the excitation light path and an Olympus DM 550, 0–515 beam splitter. A Corion (Holliston, Massachusetts) narrow band pass 530 nm interference filter was placed in the emission path in front of the photomultiplier tube to further filter excitation light. As calibrated with solutions of free fluorescein, the system was found to have a sensitivity limit of 1×10$^{-9}$ molar fluorescein. Samples were read by passing individual wells of the polystyrene 96 well microtiter plate under the microscope objective and reading the fluorescent output signal detected by the photomultiplier tube.

The results of the RIA/EPI-FIA comparison are shown in Table 1. As shown therein, the fluorescence immunoassay of the present invention had a sensitivity comparable to currently used isotopic RIA procedures even at low analyte concentrations. Accordingly, fluorescence immunoassays employing the solid supports of the present invention can be utilized for measurement of clinical analytes throughout their dynamic clinical range.

EXAMPLE 2

Assay Precision and Accuracy

In order to have an assay acceptable for clinical use, it is necessary to demonstrate a high degree of precision and accuracy. Intra-assay precision as expressed by the coefficient of variation should be less than 10% in order to be acceptable.

To demonstrate the high precisional capability of the fluorescence assays of the present invention triplicate samples of all standards were run. Two commercial controls were also run to assess the accuracy (true value) of the system.

The assay protocol, materials, and equipment of Example 1 were used with the following changes in reagent quantities and incubation times. 300 ul of solid phase (CPG) anti-ferritin antibody was employed to which was added 150 ul of sample. After a 15 minute incubation, samples were washed once with 1 ml PBS buffer and centrifuged. Supernatants were aspirated and 200 ul of a 1:10 dilution of the fluorescein labelled anti-ferritin antibody were added to each tube. Following an additional 15 minutes incubation, samples were washed once as above, reconstituted to 200 ul and read in the epifluorometer.

The results of the precision study are shown in FIG. 1. As illustrated therein, all coefficients of variation were less than 10%.

Using the same protocol and the standard curve of FIG. 1, the ferritin concentrations of the commercial controls were determined to be 12.6 ng/ml and 103.7 ng/ml. The actual value of these controls as determined by a commercial RIA procedure for ferritin were 11.1±2 and 100±14, demonstrating the accuracy of the epifluorescence immunoassay system compared to reference procedures. Findings with other serum based controls have given similar results demonstrating that serum background fluorescence does not interfere with this procedure.

It should be noted that only two 15 minute incubation steps were used to construct the standard curve of FIG. 1 and to measure the ferritin concentrations of the control samples. Commercial RIA procedures, such as the IMMOPHASE procedure of Example 1, typically require incubation periods of between about 1 and 2.5 hours to accumulate enough radioactive signal on the solid phase to achieve the desired sensitivity. This comparison shows that the epifluorescence assay of the present invention is capable of achieving more rapid test results than existing procedures, an obviously important further advantage of the system.

EXAMPLE 3

Automated Assays

This example illustrates the use of the solid supports of the present invention in an automated fluorescence immunoassay system, specifically, the SCREEN MACHINE system manufactured by Pandex Laboratories, Inc., Mundelein, Ill. It also illustrates the application of the invention to both a 2-site immunometric assay configuration and a classical competitive assay configuration.

Pandex's SCREEN MACHINE automatically performs particle concentration fluorescence immunoassays of the type described in the Jolley et al. reference and European Patent Publication No. 124,050, referred to above. As used by Pandex, the machine employs solid supports consisting of polymeric polystyrene latex particles having a diameter of approximately 0.8 microns. The device utilizes a specially designed 96 well microfiltration/microtiter plate, is microprocessor controlled, and can be programmed to add reagents and wash solutions any number of times in any desired sequence.

The SCREEN MACHINE was used to perform the 2 site immunometric assay for ferritin described above in Examples 1 and 2. The same materials as used in Examples 1 and 2 were employed. The quantities used and the incubation times employed were as follows. 30 ul of the CPG reagent were added to each well of the microtiter plate followed by 30 ul of standard. Following a 30 minute incubation step, 20 ul of a 1:10 dilution of the fluorescein labelled anti-ferritin antibody was automatically added to the wells, followed by an additional 30 minute incubation. No intermediate wash step prior to "tracer" antibody addition was performed, making the assay a one step, rather than a two step, assay as in Examples 1 and 2. At the termination of the second incubation, all wells were washed 3 times by vacuum filtration, concentrated and their epifluorescence was read.

The results are shown in Table 2 and indicate excellent precision when CPG materials are used on this automated system in an immunometric format.

In a second series of experiments, a competitive binding assay was performed utilizing commercially manufactured anti-T4 antibody coupled to CPG glass particles. Specifically, the immobilized antibody used in Ciba Corning's IMMOPHASE free T4 assay kit (Part Number 474190) was employed. The solid support used for this antibody is identical to that used in the ferritin kit, that is, it comprises borosilicate glass particles having a mean diameter of 1.5 microns, a mean pore size of 550 angstroms, and a mean surface area to mass ratio of the particles of between about 40 meter$^2$/gm and about 100 meter$^2$/gm. The immobilized IMMOPHASE antibody was concentrated 16 times by centrifugation before being used in the automated assay.

Competitive assays use labelled antigen rather than labelled antibody as "tracer". To perform this assay, a fluoresceinated T4 molecule was prepared as "tracer" utilizing carboxyfluorescein and carbodiimide conjugation procedures. A description of these procedures can be found in Lu Steffes et al., "Fluorescence Polarization Immunoassay IV. Determination of Phenytoin and Phenobarbital in Human Serum and Plasma", *Clinical Chemistry*, 28(11):2278–2282 (1982).

The assay was performed as follows. 40 ul of the concentrated IMMOPHASE antibody, 20 ul of standards or controls and 20 ul of "tracer" T4 were added to the microtiter wells. Following a 45 minute incubation, the wells were automatically washed three times and their epifluorescence was measured.

The results are shown in Table 3. Again, the solid supports of the present invention resulted in a high precision assay.

Collectively, Tables 2 and 3 demonstrate that the CPG solid phase particles of the present invention can be successfully utilized in an automated PCFIA format.

EXAMPLE 4

Epifluorescence Versus Conventional Fluorescence

This examples illustrates the superiority of performing the fluorescence assays of the present invention with epifluorescence as compared to conventional 90 degree fluorescence.

The ferritin assay of Example 1 was used to conduct the comparison, but with a sample size of 100 ul, rather than 200 ul. Conventional fluorometry was conducted by reading the suspended sample in a Perkin Elmer-Hitachi fluorometer (Model 650-40) in plastic cuvettes at an excitation wavelength of 495 nm and emission wavelength of 519 nm. Epifluorometry was performed with the apparatus described in Example 1. The sensitivity of the Perkin Elmer fluorometer was approximately 10 times less than the $1 \times 10^{-9}$ molar level measured for the apparatus of Example 1 using free fluorescein.

The results of the comparison are shown in Table 4. As can be seen from this table, the epifluorescence optical configuration easily discriminates between the 5 and 20 ng/ml samples, whereas conventional fluorometry gives the same output signal for the 5, 20, and 50 ng/ml samples. Conventional fluorometry only shows detectable differences between 50 ng/ml and 200 ng/ml.

These results demonstrate the enhanced sensitivity of the optical alignment and sample positioning in epifluorescence.

EXAMPLE 5

Particle Concentration Versus Suspension Readout

As discussed above, in the particle concentration fluorescence immunoassay technique described in European Patent Publication No. 124,050 and in the Jolley et al. reference, the polystyrene latex particles used in the assay are concentrated by microfiltration prior to having their fluorescence measured so as to increase the assay's sensitivity. As will now be shown, it has been surprisingly found that the solid supports of the present invention do not require such concentration to achieve high levels of sensitivity.

The ferritin assay of Example 1 was used to make the comparison. Samples were first read on the epifluorometer while still in suspension in 200 ul of solution. Following this reading, the particles were allowed to concentrate via sedimentation, fluid was removed and the samples were read again to determine if the concentration resulted in an increase in signal. The results are shown in Table 5.

As shown in this table, no difference in fluorescent signal after concentration of the particles was observed. Accordingly, with the CPG solid phase, concentration is not necessary prior to readout, thus making this solid phase clearly superior to a polymeric solid phase where such concentration is necessary.

EXAMPLE 6

Comparison of Physical and Optical Properties Of Latex Particles Versus Controlled Pore Glass Particles As demonstrated by the preceding example, the CPG solid supports of the present invention are superior to polystyrene latex solid supports since the CPG supports can achieve high sensitivities without being concentrated. Although not wishing to be bound by any particular theory of operation, it is believed that CPG solid supports function better than polymeric supports in fluorescence assays because they have higher surface area to mass ratios and because they are transparent at the absorption and emission wavelengths used in the assay. The present example illustrates these differences between CPG solid supports and polymeric supports.

Figure 2A:
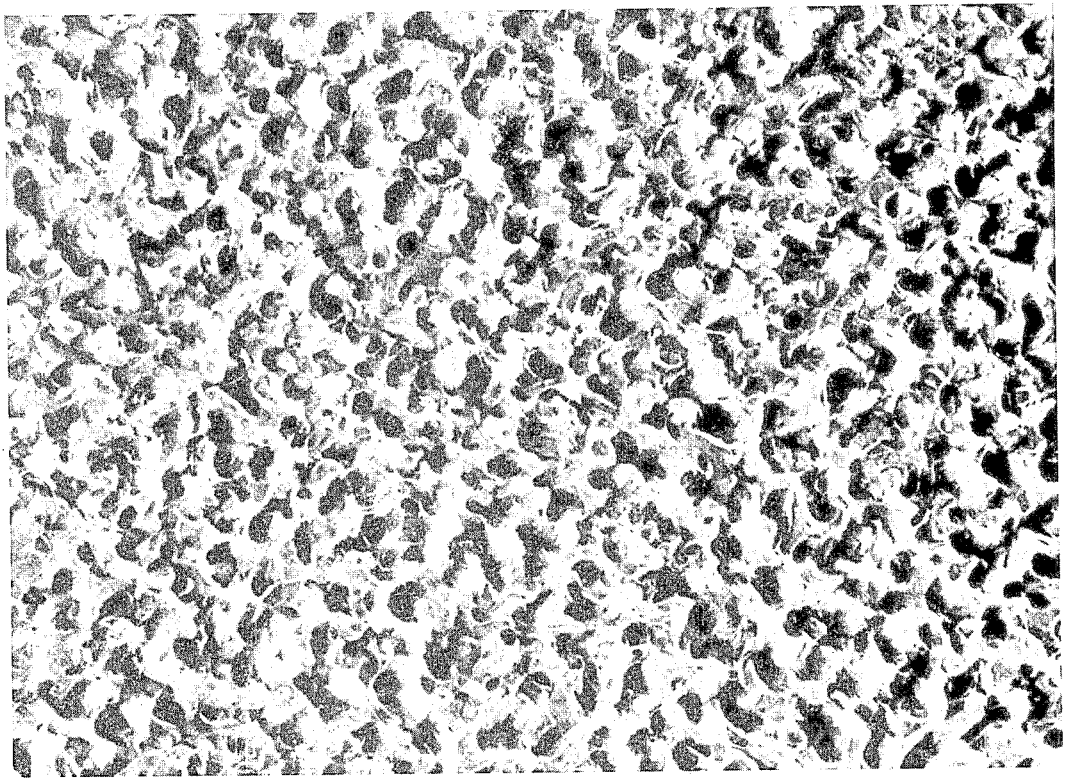
FIGS. 2A and 2B are comparative electron micrographs showing the physical differences between the controlled pore glass particles of the present invention (FIG. 2A) and latex beads of the type used in prior art fluorescence immunoassays (FIG. 2B).
Figure 2B:
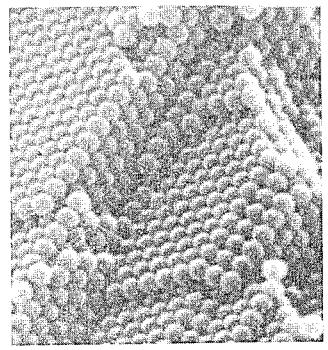

Shown in FIG. 2 are comparative electron micrographs of solid polystyrene latex spheres versus porous CPG particles of the type used in the preceding examples. As this figure demonstrates, the structure of controlled pore glass allows a larger number of "tracer" fluorophores to be concentrated into a smaller volume resulting in a greater signal strength for the same level of excitation.

The physical characteristics of CPG particles of the type used in the preceding examples, specifically, the physical characteristics of the CPG particles used in Ciba Corning's commercial IMMOPHASE products, are set forth in Table 6. The mean diameter reported in this table was measured by electronic particle sizing via voltage deflection using conventional equipment manufactured by Coulter Electronics (Hialeah, Florida), the mean pore size by mercury intrusion porosimetry using an Aminco Motor Driven 15,000 PSI Digital Readout Porisimeter, American Instrument Company, Travenol Laboratories, Silver Spring, Maryland (Catalog No. 4-7121B), the bulk density by vibrating a dry sample of the particles in a graduated cylinder to compact the particles and measuring the resulting volume and the weight of the particles, and the mean surface area/mass ratio by nitrogen adsorption. The maximum and minimum surface area/volume values were obtained by multiplying the maximum and minimum bulk density values by the maximum and minimum surface area/mass values. Ranges are given for the bulk density, mean surface area/mass and mean surface area/volume parameters since CPG is not a homogeneous material and variations are observed both within and between different batches of particles.

The comparable characteristics for solid polystyrene latex spheres having a mean diameter of 1 micron are also shown in Table 6. The bulk density given in the table is the value reported by PolySciences, Inc., (Warrington, Penn.), a manufacturer of these particles. The mean surface are to volume ratio was calculated from the formulae for the surface area and volume of a sphere ($4 \times pi \times r^2$ and $4/3 \times pr \times r^3$, respectively), evaluated for a diameter of 1 micron. The mean surface area to mass ratio was obtained by dividing the surface area to volume ratio by the bulk density.

As can be seen from Table 6, the surface area/mass ratio for the CPG particles is from 7 to 17.5 times larger than that calculated for the latex particles and the surface area/volume ratio is from 2.7 to 13 times larger. Mean values for CPG in terms of surface area/mass are on the order of 60 meter$^2$/gm, which is 10.5 times greater than the surface area/mass ratio calculated for latex particles. The surface area/volume ratios for CPG corresponding to the 60 meter$_2$/gm mean value for the surface area/mass ratio, assuming a CPG bulk density of from 0.4 to 0.8 gm/ml, range from 24 meter$^2$/milliliter to 48 meter$^2$/milliliter, which are 4 to 8 times greater than the 6.0 meters$^2$/milliliter value calculated for the latex particles.

To investigate the optical transmission properties of CPG particles compared to polystyrene latex particles, experiments were conducted using PBS buffer solutions containing the same number of particles per milliliter.

The latex particles used in these experiments were obtained from PolySciences, Inc., and had a mean diameter of 1.0 micron; the CPG particles were those used in the foregoing examples. The solutions were prepared using a hemocytometer to count the number of particles per unit volume. The particle suspensions were analyzed for light transmission at 490 nm and 525 nm, the excitation and emission wavelengths of fluorescein, using a standard spectrophotometer (Perkin Elmer Model 559A Spectrophotometer) set in % transmission mode. The results of these experiments are shown in Table 7.

As shown therein, the CPG particles are more optically transparent at the critical wavelengths of fluorophore excitation and emission than the latex particles. In terms of front face epifluorescence, this allows excitation light to pass through more particles to excite more bound fluorophore and also allows emitted fluorescent light to pass through more particles to reach the photodetector.

The foregoing observations were further evaluated in an epifluorescence format by measuring the fluorescence of free fluorescein in the presence of the polystyrene latex and CPG particles. The final concentration of particles in each case was $70 \times 10^7$ particles/milliliter of PBS buffer. The results are shown in Table 8, where each value reported is the mean of duplicate determinations. For comparative purposes, solutions of free fluorescein were also measured in the epifluorescent mode.

These results confirm that compared to latex particles, CPG particles have better optical transmission properties allowing more fluorescent signal to reach the photodetector.

TABLE 1

| | EPI-FIA vs RIA | |
|---|---|---|
| FERRITIN (ng/ml) | RIA (cpm) | EPI-FIA (relative fluorescence) |
| 5 | 2722 (1.0) | 4.1 (1.0) |
| 20 | 9833 (3.6) | 11.9 (2.9) |
| 50 | 23277 (8.6) | 25.2 (6.1) |
| 200 | 54297 (19.9) | 91.3 (22.2) |
| 500 | 75066 (27.5) | 139.3 (33.9) |
| 1000 | 83360 (30.6) | 157.3 (38.3) |

Numbers in parentheses are the ratio of signal at a given concentration of standard to that of the 5 ng/ml concentration standard and offer a basis for comparison at different ferritin analyte concentrations. The output signal for 0 ng/ml has been subtracted out of both the RIA and the FIA values to correct for non-specific signal. Results are the mean of duplicate determinations.

TABLE 2

| Utilization Of CPG Solid Phase Anti-Ferritin Antibody On An Automated Epifluorometer In An Immunometric Assay Format | | |
|---|---|---|
| FERRITIN (ng/ml) | EPIFLUORESCENCE (Run #1) | EPIFLUORESCENCE (Run #2) |
| 0 | 1166 | 1106 |
| 5 | 1306 | 1466 |
| 20 | 1616 | 1592 |
| 50 | 2566 | 2278 |
| 200 | 4944 | 4624 |
| 500 | 7346 | 7380 |
| 1000 | 8548 | 8602 |

TABLE 3

Utilization Of CPG Solid Phase
Anti-T4 Antibody On An Automated
Epifluorometer In A Competitive Binding Assay Format

| T4 (ug/dl) | EPIFLUO-RESCENCE (Run #1) | EPIFLUO-RESCENCE (Run #2) | COEFFICIENT OF VARIATION |
|---|---|---|---|
| 0.0 | 11460 | 12954 | 8.6% |
| 1.25 | 11434 | 10874 | 3.6% |
| 2.5 | 10680 | 10346 | 2.2% |
| 5.0 | 9776 | 9390 | 2.8% |
| 10.0 | 7828 | 7668 | 1.5% |
| 15.0 | 6444 | 6484 | 0.4% |
| 30.0 | 4982 | 4670 | 4.6% |

TABLE 4

Epifluorescence Versus Conventional Fluorescence

| FERRITIN (ng/ml) | EPIFLUORESCENCE | FLUORESCENCE |
|---|---|---|
| 5 | 3.1 (1.0) | .009 (1.0) |
| 20 | 7.7 (2.5) | .009 (1.0) |
| 50 | 13.8 (4.5) | .009 (1.0) |
| 200 | 58.5 (18.9) | .032 (3.5) |
| 500 | 107.5 (34.7) | .070 (7.8) |
| 1000 | 146.5 (47.2) | .104 (11.5) |

Numbers in parentheses are the ratio of signal at a given concentration of standard to that of the 5 ng/ml concentration standard and offer a basis for comparison at different ferritin analyte concentrations. The output signal for 0 ng/ml has been subtracted out of the values reported to correct for non-specific signa. Results are the mean of duplicate determinations.

TABLE 5

Epifluorescence Of Suspended Versus Concentrated Particles

| FERRITIN (ng/ml) | SUSPENDED PARTICLES | CONCENTRATED PARTICLES |
|---|---|---|
| 5 | 4.8 | 6.6 |
| 20 | 12.6 | 11.6 |
| 50 | 25.9 | 24.5 |
| 200 | 92.0 | 88.5 |
| 500 | 140.0 | 132.0 |
| 1000 | 158.0 | 152.0 |

The output signal for 0 ng/ml has been subtracted out of the values reported to correct for non-specific signal. Results are the mean of duplicate determinations.

TABLE 6

Comparisons of Physical Characteristics of Latex Spheres Versus Control Pore Glass Particles

| CHARACTERISTIC | LATEX | CPG |
|---|---|---|
| Mean diameter (microns) | 1.0 | 1.5 |
| Mean pore size (Angstroms) | none | 550 |
| Bulk density (gm/ml) | 1.05 | 0.4–0.8 |
| Mean surface area/mass (m$^2$/gm) | 5.71 | 40–100 |
| Mean surface area/volume (m$^2$/ml) | 6.00 | 16–80 |

TABLE 7

Comparisons of Optical Transparency of Suspensions of Latex and CPG Particles

| PARTICLES/ML OF BUFFER ($\times 10^7$) | CPG % TRANS-MISSION 490 nm | CPG % TRANS-MISSION 525 nm | LATEX % TRANS-MISSION 490 nm | LATEX % TRANS-MISSION 525 nm | RATIO CPG:LATEX 490 nm | RATIO CPG:LATEX 525 nm |
|---|---|---|---|---|---|---|
| 140 | 4.3 | 6.9 | 0.1 | 0.1 | 43 | 69 |
| 14 | 73.1 | 76.2 | 15.6 | 19.3 | 4.6 | 3.9 |
| 1.4 | 97.4 | 97.8 | 86.4 | 88.0 | 1.1 | 1.1 |

Particles were adjusted to the same number of particles/ml PBS buffer and optical transmission measured on a Perkin Elmer Model 559A Spectrophotometer set in the % transmission mode.

TABLE 8

Comparison Of Epifluorescent Signal Attenuation By CPG And Latex Particles In Solutions Of Free Fluorescein

| FLUORESCEIN | CPG SIGNAL | LATEX SIGNAL | FREE FLUORESCEIN SIGNAL |
|---|---|---|---|
| $10^{-5}$ Molar | 55600 | 33290 | 62000 |
| $10^{-6}$ Molar | 5790 | 4340 | 7390 |
| $10^{-7}$ Molar | 487 | 352 | 646 |
| $10^{-8}$ Molar | 49 | 35 | 59 |
| Buffer | 1.9 | 1.4 | 2.0 |

What is claimed is:

1. In a heterogeneous fluorescence assay wherein a ligand/ligand-binding-partner complex is formed on a solid support, the ligand or ligand-binding-partner including a fluorescent probe, and fluorescence is measured by exciting the probe with light of a first wavelength and sensing the light emitted by the probe at a second wavelength, the improvement comprising using as the solid support controlled pore glass particles which are substantially transparent at the first and second wavelengths.

2. The heterogeneous fluorescence assay of claim 1 wherein the controlled pore glass particles have a mean pore size of between about 400 angstroms and about 800 angstroms, a mean diameter of between about 0.7 microns and about 3.0 microns, and a mean surface area to mass ratio of at least 40 meter$^2$/gram.

3. The heterogenous fluorescence assay of claim 2 wherein the controlled pore glass particles have a mean surface area to mass ratio of between about 40 meter$^2$/gram and about 125 meter$^2$/gram.

4. The heterogeneous fluorescence assay of claim 3 wherein the controlled pore glass particles are composed of borosilicate glass, have a mean pore size of about 550 angstroms, a mean diameter of about 1.5 microns, and a mean surface area to mass ratio of between about 40 meter$^2$/gram and about 100 meter$^2$/gram.

5. The heterogeneous fluorescence assay of claim 1 wherein the fluorescence of the probe is measured using front face epifluorometry.

6. The heterogeneous fluorescence assay of claim 5 wherein the epifluorometry is performed on the particles suspended in buffer.

7. The heterogeneous fluorescence assay of claim 1 wherein the ligand is an antigen and the ligand-binding-partner is an antibody.

* * * * *